United States Patent [19]

Miwa et al.

[11] Patent Number: 4,757,715
[45] Date of Patent: Jul. 19, 1988

[54] APPARATUS FOR CHARACTERIZING ULTRASONIC MEDIUM

[75] Inventors: Hirohide Miwa; Keiichi Murakami, both of Kawasaki; Takaki Shimura, Machida; Yutaka Igarashi, Yokohama; Akira Shiba, Kawasaki; Hajime Hayashi, Yamato, all of Japan

[73] Assignee: Fujitsu Limited, Kawasaki, Japan

[21] Appl. No.: 16,472

[22] Filed: Feb. 17, 1987

Related U.S. Application Data

[63] Continuation of Ser. No. 768,120, Aug. 13, 1985, abandoned.

[30] Foreign Application Priority Data

Dec. 14, 1983 [JP] Japan .................. 58-235852

[51] Int. Cl.$^4$ ........................................... G01N 29/00
[52] U.S. Cl. ........................................ 73/602; 73/599; 128/660
[58] Field of Search .................. 73/599, 602, 620, 629, 73/631; 128/660

[56]  References Cited

U.S. PATENT DOCUMENTS

| | | | |
|---|---|---|---|
| 4,016,750 | 4/1977 | Green | 73/629 |
| 4,197,750 | 4/1980 | Hassler | 73/629 |
| 4,470,303 | 9/1984 | O'Donnell | 73/602 |
| 4,509,524 | 4/1985 | Miwa | 73/599 |

Primary Examiner—John Chapman
Attorney, Agent, or Firm—Staas & Halsey

[57] ABSTRACT

The present invention relates to a signal processing apparatus for quantitatively measuring ultrasonic characteristics of a medium, such as a human body and realizes the high speed quantitative measurement by processing all signals in the time domain. In the processing for eliminating an error, produced by a degree of convergence of the ultrasonic beam, a correcting function that is a function of the depth and frequency is employed. The correcting function is measured in a no-attenuation medium and converted into a form suited to the time domain processing. The function is stored and such frequency characteristics of the function are sequentially read during an actual medium measurement to control the characteristic of a variable characteristic filter to correct the received signal.

5 Claims, 2 Drawing Sheets

APPARATUS FOR CHARACTERIZING ULTRASONIC MEDIUM

This is a continuation of co-pending application Ser. No. 768,120 filed on 8-13-85, now abandoned.

BACKGROUND OF THE INVENTION

The present invention relates to an apparatus for quantitatively measuring characteristic values of a medium by sending an ultrasonic wave pulse into a medium such as a human body, etc., receiving the pulse wave sequentially reflected from respective depths and by processing such received signal, and particularly, to a signal processing system where spectrum error resulting from the fact that a degree of convergence (divergence) of the ultrasonic beam changes non-uniformly as a function of the depth of the medium can be corrected on realtime basis in the time domain without obtaining the shape of the spectrum by FFT, etc.

First, changes in the convergence of the ultrasonic beam dependent on the depth of the medium will be explained. In FIG. 1(a), 1 denotes an ultrasonic wave transducer consisting of a piezoelectric element such as PZT, etc. and 2 is a medium such as a human body. The primary ultrasonic pulse sent from the transducer 1 travels in the depth direction (z-axis direction in the figure) of the medium, secondarily generating waves reflected from the medium at respective depths and finally disappears. The reflected waves from respective depths travel in a direction opposite to the primary pulse and are received by the transducer 1. A wave reflected from the shallow area with a small value of z reaches the transducer quickly but a wave reflected from the deep area with a large value of z reaches with a delay. Therefore, the received signal has a continuous waveform. The characteristic values of a medium such an ultrasonic wave attenuation coefficient, etc., of living body tissue can be obtained by processing the received signal. It is obvious that the attenuation coefficient is proportional to frequency in living body tissue, etc., and this proportional coefficient is called a slope of attenuation coefficient and therefore, it is often used as a characteristic value of the medium.

As explained above, when the primary ultrasonic pulses used are reflected from a certain depth in the same medium, the shape of the spectrum and intensity of the wave is always assumed to be constant irrespective of the depth in order to check the frequency characteristic of the medium, that is, there is no attenuation in transmitting function of medium and it does not depend on frequency.

In actual practice, however, the shape of ultrasonic beam formed depending on the sending and receiving sensitivity of ultrasonic pulse is not constant as a function of depth with respect to some frequency components and changes, as shown in FIG. 1(a). Moreover, a sound pressure along the center axis is distributed, as shown in FIG. 1(b). The beam also includes, as indicated by a dotted line shown in FIG. 1(a), other frequency components and therefore, a sound pressure on the center axis is distributed with an actual difference from that of FIG. 1(b). This is because the degree of convergence (namely, degree of divergence) of beam changes geometrically in three dimensions If this effect is neglected, a large error is introduced into the distribution in the depth direction of the measured characteristic values of the medium.

To correcting such an error, the inventors have proposed the following system (*1: Miwa et al., Japanese laid-Open Pat. No. 58-55850, corresponding to U.S. Pat. No. 4,509,524).

In this system, a reference medium like water, which has attenuation so small that it can be neglected (it is desirable that the acoustic impedance and sound velocity are as similar as possible to the medium to be measured but if there is a difference, it can be allowed for) is used. The ultrasonic pulse is transmitted from the transducer, the reference reflector (a solid flat plate or ball having smooth or rough surface) is placed at various depths z (where distance between the transducer and reflector on the beam line of the transducer is z), and the respective reflected waves are received and spectrums Sz(f) are also obtained where f represents frequency A reference depth, $z_0$, for example, near the focus shown in FIG. 1, is designated and the spectrum of reflected wave at the depth $z_0$ is $S_{z0}(f)$. In the spectrum domain, $Sz(f)^2$ is standardized as $S_{z0}(f)^2$. A value Gz(f) obtained from the standardization is called a geometrical factor (G factor) and is defined as indicated below.

$$Gz(f) = |Sz(f)|^2 / |S_{z0}(f)|^2 \tag{1}$$

$|S'z(f)|^2$ is defined as the power spectrum as defined by the equation (2).

$$|S'z(f)|^2 = |Sz(f)|^2 / Gz(f) \tag{2}$$

In this definition, S'z(f) has the same spectrum shape and intensity, namely $S_{z0}(f)$, at all depths. An error due to the geometrical factor can be corrected by measuring the processing characteristic values of the medium through investigation Concerning how S'z(f) changes in accordance with the medium being measured.

The concept for correction with respect to media is introduced into a successive application (*2: Miwa, Japanese Patent Application No. 57-57573) and the relationship indicated in equation (3) below, is used in place of the equation (1) and on the power function.

$$Gz = \frac{\int |Sz(f)|^2 df}{\int |S_{z0}(f)|^2 df} \tag{3}$$

This concept was applied in two other patent applications (*3: Miwa, Ueda, Japanese Patent Application No 57-129902, Miwa et al., corresponding to U.S. patent application Ser. No. 477,935, filed in 1983) and was an aspect of diffraction correction in the following three reference papers given at the Eighth International Symposium on Ultrasonic Imaging and Tissue Characterization, June 5-8, 1983; Ultrasonic Imaging 5, P. 186-187 in June, 1983.

*5 (D. W. Pettibone et al., Diffraction effects on the measured spectrum of a focused acoustic transducer)

*6 (Cloosterman, J. M. Thijsen et al., IN VITRO absolute attenuation measurement with diffraction correction)

*7 (M. Fink et al., Influence of diffraction effects on the estimation of the tissue attenuation by spectral analysis of A-lines)

However, the references *3, *4, *5, *6 and *7 all describe signal processing in the frequency domain and correction of diffraction effects in the frequency domain. The reference *7 reports on a simplified approximating method where the center frequency is obtained accurately from the center frequency of the spectrum divided by Gz(f) to correct the center frequency obtained from the power spectrum. In this method, water is used as no-attenuation medium and the deviation of the center frequency of the spectrum Sz(f) of the signals reflected from respective depths from the center frequency of spectrum $Sz_0(f)$ of the reference depth $z_0$ is obtained and the deviation is added to the center frequency of the received signal at the respective depths obtained from the medium to be measured to perform the correction. This method is equivalent to an approximate multiplication in which any errors inevitably increase in magnitude.

In the reference *2, since the focus of the application is on power, the bandwidth of a wideband pulse is divided into n-domains (n>3) or into n different frequency power components, consideration is taken for the geometrical factor in the power region but the shape of spectrum (in case n is sufficiently large) is not used or considered. When a sufficiently large n is used, conversion to the frequency domain by using an FFT, etc., is also necessary. This is an intermediate method between the frequency region method and the time region method described later.

When n is large in devices of the references *3, *7 and *2, the geometrical factor (G factor) or diffraction effect is corrected in the frequency domain during signal processing in the frequency region, and it requires that the waveform on the time axis be extracted using a time window (of window width T) around a certain point (t=2z/C corresponding to the depth z at the sound velocity C), the waveform is then converted into frequency domain data through a Fourier transform, and correction of G factor along with signal processing for extracting the attenuation coefficient slope are carried out. Therefore, a disadvantage arises in that a finite processing time is required even when an FFT (Fast Fourier Transform) circuit and other circuits are used, and, as a result, the received signal is not suited to real-time processing. Moreover, the FFT and other circuits are complicated, large in size and expensive.

The same inventors as in the present invention proposed a signal processing system where characteristic values of a medium are extracted from the received signal in the time region without converting it to the frequency region (*2, *8 and *9).

The reference *8 (Miwa et al., Japanese Laid-Open Patent No. 57-550) performs out signal processing in the time region on the received reflected power and obtains the attenuation slope of the medium. In this application, the reflectivity does not have a frequency characteristic of interest. In the frequency region, power is the 0th order moment of the power spectrum and is naturally influenced by the G factor. However, this factor is not considered in this application.

As is already explained, the reference *2 is capable of executing signal processing only in the time domain when n is 3. Although correction using the G factor is considered, the G factor takes the form of equation (3) instead of equation (1) because attention is only on the power as is the case in reference *8. As explained above, it is sufficient for the application field of the references *2 and *8 to use an amount correction only for integral values in the bandwidth as a whole, and the error due to so-called spectrum scalloping cannot be corrected in the references *2 and *8. The reference *9 can likely correct scalloping error in the time region system.

The reference *9 (Shiba et al., Japanese Patent Application No. 58-77226) discloses that the 0th, 1st, 2nd, 3rd, ... moments of power spectrum are obtained from the in-phase component I and quadrature component Q of a quadrature detector output. This reference describes extracting characteristic values of the medium from these moments, using a simplified structure, reduced in size, cost and real-time processing.

It is necessary for correct medium characterization to correct for the G factor, even in reference *9, however, such a correction has not been reported yet in the art.

SUMMARY OF THE INVENTION

It is an object of the present invention to provide a simplified, small size, high precision and economical apparatus for measuring characteristic values of a medium which realizes high speed signal correction on a real-time basis by providing a system that performs correction in the time region and allows scalloping corrections by converting a correction signal into the frequency region and correcting the geometrical (G) factor resulting from a three-dimensional change in ultrasonic beam focusing in dependence on the depth.

The present invention inputs a received reflection signal, as a function of time t corresponding to the depth in the medium, into a filter which changes its frequency filtering characteristics with time so that a G-factor correcting coefficient corresponding to time (depth) is produced and a time corrected reflection signal is the output of the filter.

DESCRIPTION OF THE PREFERRED EMBODIMENTS

Figure 2:
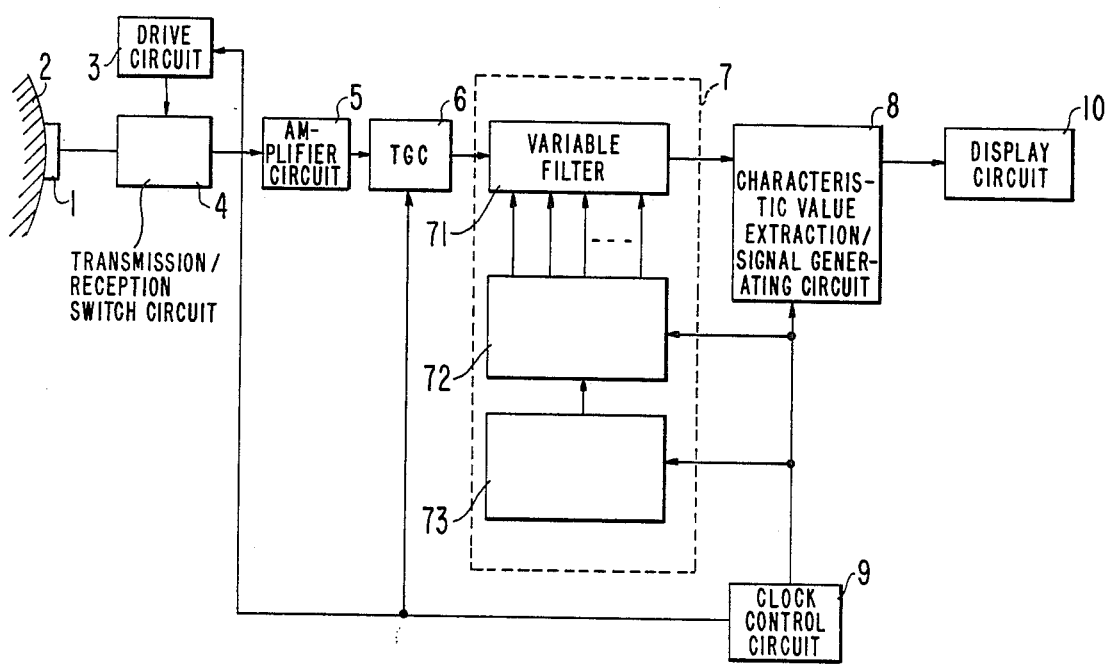
FIG. 2 is a block diagram of an essential part of an embodiment of the present invention.

FIG. 2 is a block diagram of an embodiment of an essential part of the apparatus for measuring characteristic values of an ultrasonic medium to which the present invention is applied. In addition to the circuits shown in FIG. 2, the circuits for two-dimensional scanning of an ultrasonic beam and the circuits for displaying the two-dimensional distribution image of characteristic values of medium obtained by such scanning can also be added.

2 is a medium to be measured, such as a living body. 1 is a piezoelectric transducer made of PZT, etc. 3 is a circuit for generating a voltage pulse to drive the transducer 1 to generate the ultrasonic pulse. Generally, an ultrasonic pulse including having center frequency of 2-5 MHz is generated. 4 is a switch for transmission and reception switching which connects the transducer 1 to the drive circuit 3 during transmission of the ultrasonic pulse, and to the amplifier 5 after the transmission, thereby receiving the reflected wave from the medium. 5 is a wideband amplifier. When the sending center frequency is set at 3 MHz, for example, bandwidth of receiving pulse generally ranges from 2 to 4 MHz. is amplifier 5 provides a bandwidth of 2-4 MHz along with a sufficient margin. 6 is a wide band amplifier which controls amplification with respect to time and is called a TGC (Time-Gain-Control) circuit or STC (Sensitivity-Time-Control) circuit, etc. A signal reflected from deeper in the medium is more greatly attenuated along the propagation path and the received signal is smaller in amplitude. Therefore, this amplifier 6 has the lowest gain immediately after the signal is transmitted and thereafter, gradually increases the gain with time. The degree of gain increase can be controlled manually or automatically, so that an output of amplifier 6 is always maintained at the optimum level for signal correcting through filter adjustment processing. This amplifier is necessary for optimizing the S/N of system so that a sufficient dynamic range is obtained, where S/N is a ratio of the maximum input signal to a correcting filter 7 to the noise in signal. The amplifier 6 must always be provided in a stage preceding the correcting filter 7. Units 71, 72, 73 form a correcting filter 7. 8 is a signal processor (including a program controlled micro-computer, etc.) which processes the corrected signal and extracts characteristic values of the medium, such as attenuation coefficient slope of a living body tissue. 9 is a clock controller which generates the clock and timing signals for operations explained above and also controls the system as a whole. 10 is a unit, such as a display or recorder, which provides information to operators.

It is sufficient for the signal processor 8 to execute the processing discussed in the reference *9 mentioned above and the characteristic values of the medium can be obtained as a function of depth on a real-time basis only in the time domain without conversion to the frequency region. Processing by signal processor 8 is not part of the present invention. The processor 8 may be replaced by a circuit such as FFT circuit which converts the corrected signal into the frequency region and processes the signal in the frequency region. In such a case, a correction of the G factor is carried out on a real-time basis in the time domain and the processing time can be reduced; however, the reduction is not great, as compared to the successive processing time for image production.

Figure 1:
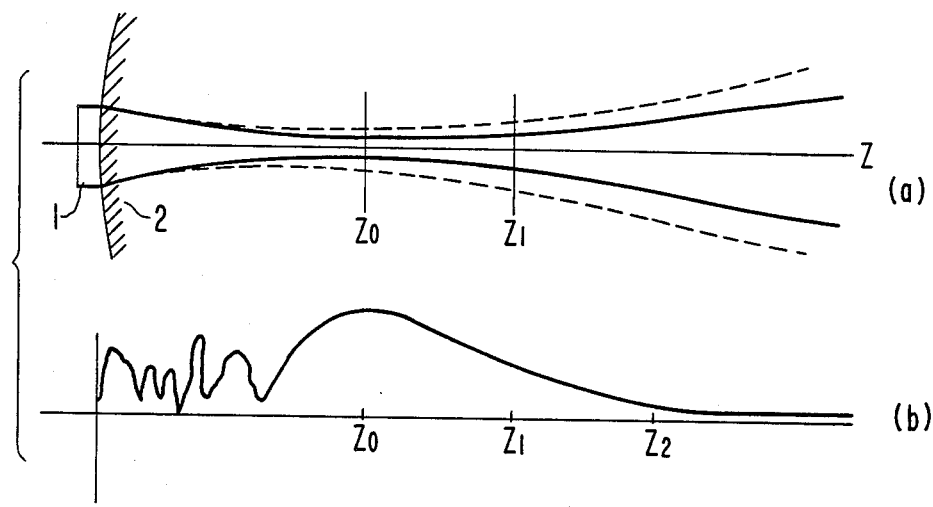
FIG. 1 shows three-dimensional changes of shape and intensity of an ultrasonic beam in a medium.
Figure 3:
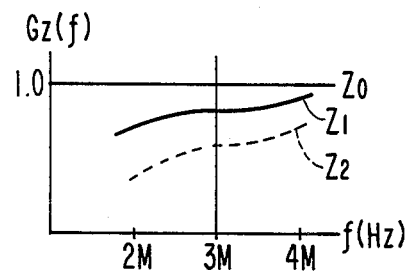
FIG. 3 is a frequency characteristic wherein depth of the G factor is changed as the parameter.

The received signal correcting filter 7 which is the gist of the present invention, will be explained in detail. FIG. 3 shows the shape of the G factor $Gz(f)$. From the definition of equation (1), $Gz_0(f) = 1$. If the reference depth $z_0$ is selected as the maximum sound pressure point on the center axis, as shown in FIG. 1(b), the G factor is smaller than the absolute value of the spectrum in the other deeper areas $z_1$, $z$ and the shallower area $z$ ($<z_0$). Therefore, $Gz(f)$ changes shape as a function of $z$ as indicated with respect to $z=z_1$ and $z=z_2$. $Gz(f)$ can be defined only in the bandwidth of interest (for example, 2~4 MHz) where sufficient signal spectrum strength exists and must not be produced from other parts of the bandwidth because other parts of the spectrum will be a noise component.

A square root value of the inverse $Gz(f)$ gives a correction coefficient for the spectrum. A square root value is obtained because $Gz(f)$ is defined with based on power. If $Gz(f)^{-1/2}$ is written as $Uz(f)$ times a value of $a_z$, the correction coefficient at a certain frequency $f_0$ can be expressed as follows:

$$1/[Gz(f)^{1/2}] = a_z \cdot U_z(f) \qquad (4)$$

where $a_z$ is a constant value depending on the depth $z$ and is a gain having no frequency characteristics. $Uz(f)$ represents only frequency characteristic component of the spectrum.

The filter 7 must have the characteristic shown by the equation (4), however, it is convenient to control $a_z$ in combination with the TGC 6 and control the frequency characteristics with the filter 7. In this case, since $a_z$ can be obtained from a previously measured $Gz(f)$ as a function of $z$, namely as a function of time and it can also be stored, when the gain of TGC 6 is measured as a function of time, a difference between the TGC gain and the correction coefficient gain $a_z$ is the gain required for correction of attenuation and therefore it can be used as the attenuation data as required.

Figure 4:
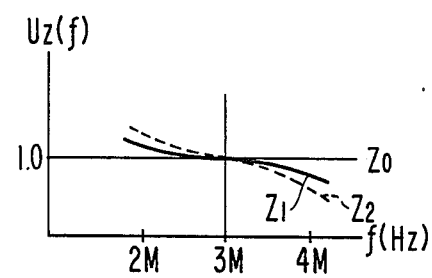
FIG. 4 is a frequency characteristic of the frequency characteristic portion Uz(f) of a G factor correcting term.

Hereinafter, the correcting filter 7 will be assumed to execute the correction $Uz(f)$ only for the frequency characteristics. $Uz(f)$ for $z=z_0$, $z_1$ and $z_2$ are shown in FIG. 4.

The variable filter 71 can be realized by a circuit combining inductance L, capacitance C and resistance R which are variable with voltage or current with a fixed L, C, R. As an example of such elements, an unsaturated reactor which is variable using a DC voltage, a variable capacitance diode and a MOS transistor can be used. Here, it is also supposed that such voltage controllable parameter elements (variable L, C, and R) are used in a number n. The frequency characteristic of a filter 7 which changes with time, as shown in FIG. 4, can be thus realized by applying a programmed voltage which changes with time to n parameter control terminals.

Figure 5A:
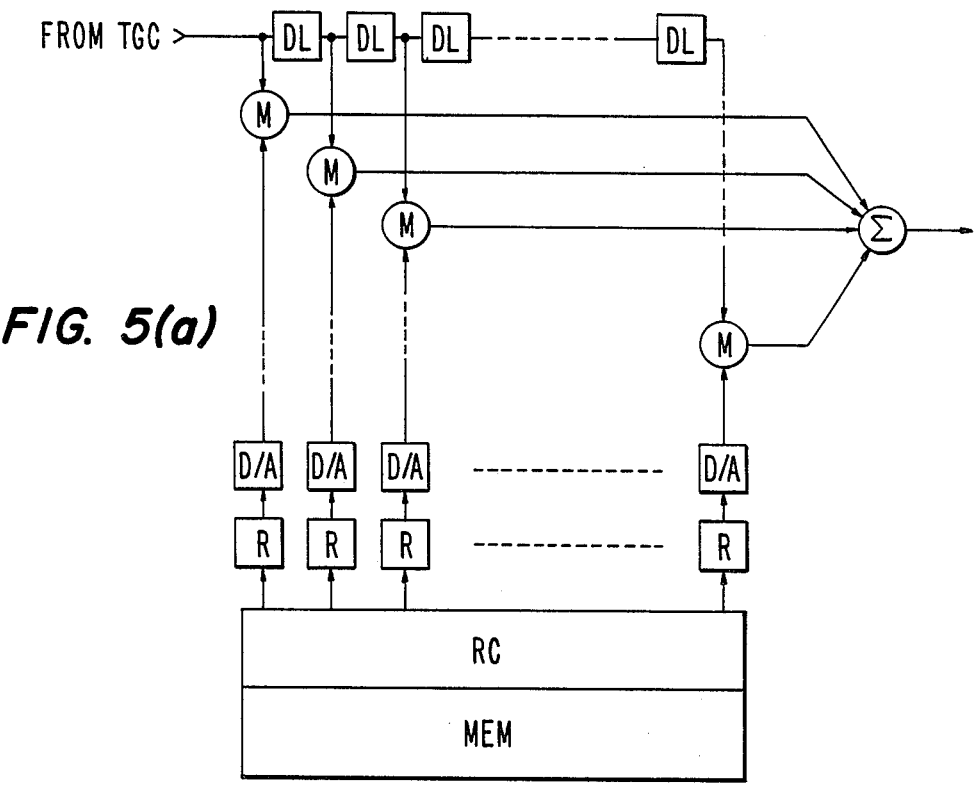
FIGS. 5(a) and 5(b) are block diagrams of an embodiment of the present invention utilizing a convolutional integral filter.

Unit 73, in FIG. 5(a) is a correction coefficient-parameter conversion storage unit which stores the n parameter voltages previously calculated to produce Uz(f) corresponding to depth, namely to time (as a function of time) and this circuit can be a microcomputer and ROM, RAM, etc., if voltage is digitized.

Unit 72 is a parameter read circuit which sequentially reads digital values of parameter control voltage corresponding to the time from the circuit 73 in accordance with the timing signal sent from the circuit 9 and generates the n parameter control voltages through a D/A conversion.

As explained above, the correcting filter 7 composed of the circuits 71, 72 and 73 realizes the time varying characteristics of the correction function Uz(f).

The necessity of storing the correction coefficients (or parameters) as a continuous function of time results in a large amount of storage capacity being required for the circuit 73, and this increases the size and the price of the system. To reduce the costs, the changes of Uz(f) with respect to time can be approximated by changes in the form of a staircase. Namely, Uz(f) is changed using a fine time step during the range of sudden changes in the spectrum, while a coarse time step is used for the range of gradual spectrum changes. Using this method, the required storage capacity can be drastically reduced.

If a filter requires a longer period for switching between Uz(f) values in accordance with time, a plurality of filters can be provided, one filter is switched to the next value at Uz(f) while another filter is being used for actual filtering and such filters can be used alternately or sequentially. In such a case, the outputs can be switched while the inputs to the filters are in common or the inputs can be switched while the outputs are in common.

In the above embodiment, the filter is an analog filter utilizing analog elements, such as L, C, and R. However, a digital filter can be used formed of an A/D conversion unit, a digital processing unit, a D/A conversion unit. For an analog filter, it is difficult to design the phase characteristics in the frequency region, and an error is not generated when the corrected signal is employed in the system of reference *7 where the emphasis is placed in the moment of the power spectrum. An error is generated in a system in accordance with reference *8 using the corrected signal where emphasis is placed on the phase. If a digital filter is employed in the system of reference *8, the rotation of phase in the filter can be eliminated.

Figure 5B:
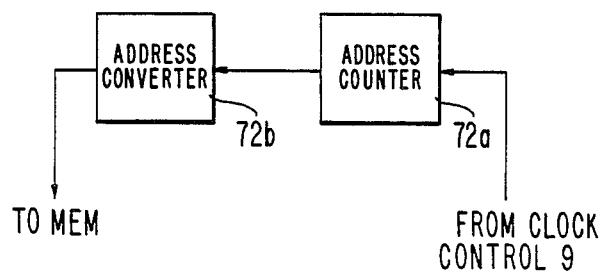

In another embodiment of the filter 7, a convolution type filter will be explained with respect to FIG. 5(a). It is used as a replacement of the correcting filter 7 consisting of the circuits 71, 72 and 73 shown in FIG. 2. DL is a delay element and the required delay time $\delta$ may be 50–100 ns when the center frequency of ultrasonic pulse is 3 MHz, M is an analog multiplication circuit, D/A is a digital-to-analog conversion circuit, R is a register, MEM is a digital memory and RC is a read controller which reads a set of correcting data from the memory MEM as required and loads the data into all registers R. RC is explained in further detail with respect to FIG. 5(b). This read controller RC includes an address counter 72a which advances sequentially based on the clock from the clock controller 9 (FIG. 2) and an address converter 72b which determines the speed of change of the filter based on receiving an output from the address counter 72a. Returning to FIG. 5(a) for explanation, $\Sigma$ is an adder and operations are explained below.

If the spectrum of a signal i(t) input into the filter is assumed as I(f), an output O(t) of the filter is determined by the inverse Fourier transform of a product of I(f) and Uz(f). When the inverse Fourier transform of Uz(f) is defined as uz(t) in accordance with the theory of mathematics, O(t) is produced by the convolution of i(t) and uz(t).

The waveform of uz(f) for each z, namely, for the time step is stored in the MEM using a time step $\delta$ for the z of the required step and the waveform uz(t) corresponding to z is read as a unit and is stored in the register R. The digital value being stored in the register is converted to an analog value, it is then multiplied with input signals delayed respectively, by $\delta$ of the DL circuits, and all multiplied outputs are added by the adder $\Sigma$. The above operations represent just the convolution of input i(t) and time waveform uz(t) obtained by Fourier transform of the correction coefficient Uz(f). Uz(f) has a bandwidth of several MHz and uz(t) is the waveform about several microseconds in length and, as a result, the number of DL, M, D/A and R units can range from several tens to a hundred. Recent LSI's available on the market integrate about 128 elements including the units DL, M, D/A and R and thereby are reduced in size and cost. However, the signals in these circuits cannot be input in parallel to registers R but in series and therefore loading time and the switching time of z are long. However, this problem can be solved by also employing the method for sequentially switching a plurality of pairs of filters, discussed previously.

The present invention can be combined with other correction methods for correcting, for example, center frequency, as discussed below. When the send pulse has a gaussian distribution spectrum $S_0(f)$ with a center frequency $f_0$ and divergence $\delta$, the medium to be measured is a living body tissue such as a human body and attenuation coefficient is $\alpha (z) = \beta(z)f$ (where $\beta$ is a proportional constant), it is well-known that the spectrum of the waveform reflected from a particular depth z deviates, by an amount set forth in equation (5), at the center frequency $f_z$ and shape $S_z(f)$ of spectrum is a gaussian distribution of this divergence.

$$f_0 - f_z = 4\sigma^2 \int_0^z \beta(z)dz \tag{5}$$

This equation indicates that the depth and the center frequency $f_z$ are functionally related. When Uz(f) is corrected, the actual uncorrected spectrum Sz(f) does not include the deviated gaussian distribution and, as a result, the center frequency is further deviated by $\Delta f_z$. This deviation can be calculated as the function of z and $f_z$. In the system described in reference *9, $f_z$ can be measured as the function of z, namely, as the function of time. Therefore, when fz, is obtained, a corrected fz can be obtained by previously calculating an amount of correction for fz and the correction can be performed using correction values stored in a table. A correct distribution of $\beta(z)$ can also be obtained in this manner, That is, the present invention which corrects spectrum shape can be improved to correct not only the spectrum of the received signal but also the center frequency and the distribution $\beta(z)$.

In the above example, the center frequency $f = f|S(f)|^2 df/ |S(f)|^2 df$ itself is used as the typical parameter to be measured after the reflected signal is corrected but the bandwidth or other parameters may be used also as the typical parameter to be measured. The shape of spectrum is not corrected but the center frequency is moved. The following explanation will discuss allowable changes in the shape of the spectrum which are in a 1:1 relationship to the typical parameter. When a typical parameter is to be measured as a function of depth, the corrected spectrum can be obtained corresponding to a certain depth and G factor correcting coefficient. The center frequency correction and after correction amount, such as the moments are obtained from the corrected spectrum, as the function of depth from a relationship of the measured typical parameter (reference value) and the depth measured value. As a result, because the other corrections are based on a corrected spectrum, an accurately corrected distribution with respect to depth of other characteristic values of the medium, such as the attenuation coefficient slope, etc., can be obtained.

The method of FIG. 5 produces the correction by correction multiplication operation using repetitive and similar simplified steps. The multiplication method is similar to the method of addition correction of the center frequency discussed in reference *7 and however, it produces a more accurate characterization of the medium since the entire spectrum is corrected.

According to the present invention, the G factor which is a distortion of the spectrum resulting from three-dimensional nonuniformity in the degree of convergence of ultrasonic beam can be corrected in the time region without a Fourier transform of received signal in such a form which also realizes the correction of spectrum scalloping. Accordingly, a simplified, small size and economical apparatus for measuring characteristic values of an ultrasonic medium can be obtained for a highly accurate and high speed real time characterization.

We claim:

1. An apparatus for measuring characteristic values of a medium to be measured which quantitively measures characteristic values of the medium by sending an ultrasonic pulse into the medium, receiving reflected signals, having gain and frequency characteristics, reflected from respective depths of said medium as a function of time, and processing the received signals, said apparatus comprising:

storing means for storing, as a function of time corresponding to depth, spectrum correction information for continuously correcting changes of a spectrum shape of the entire received reflected signal by changing the frequency characteristics of the received reflected signal, and changes of intensity of the received reflected signal by changing the gain characteristics of the entire received reflected signal, said changes to the spectrum and intensity resulting from a three dimensional change of convergence and diffraction of an ultrasonic beam as a function of depth, obtained by utilizing the spectrum of reflected reference signals reflected from reference reflectors placed at respective depths of a medium which shows attenuation small enough to be neglected; and correcting means for correcting, in a time domain, in accordance with the respective spectrum correction information sequentially read from said storing means, the shape of the spectrum of the reflected signal, received as a function of time, from said medium to be measured, said correcting means including a correcting amplifier which receives the received reflected signal and has a variable gain characteristic, and a correcting filter having a variable frequency characteristic, the variable gain characteristic and the variable frequency characteristic being controlled by the respective spectrum correction information from said storing means.

2. An apparatus for measuring characteristic values of an ultrasonic medium according to claim 1, wherein said correcting filter is a digital filter comprising an A/D converter, a digital processing circuit connected to said A/D converter and a D/A converter connected to said digital processing circuit.

3. An apparatus for measuring characteristic values of an ultrasonic medium according to claim 1, wherein said storing means stores, as the spectrum correction information, time waveform information which is obtained by an inverse Fourier transform of the spectrum of the reference reflected signals, where the frequency characteristic of said correcting filter is derived from the spectrum and said correcting filter comprises means for performing a convolution of the received reflected signal and said time waveform information.

4. An apparatus for measuring characteristic values of an ultrasonic medium according to claim 3, further comprising a time gain control circuit and wherein said correcting filter is connected in series with said time gain control circuit for correcting only gain and said filter for correcting only frequency characteristics.

5. An ultrasonic measurement device for measuring characteristic values of a medium to be measured, comprising:

means for sending ultrasonic pulses into said media;
means for receiving reflected signals having spectrum shapes and gain characteristics;
storing means for storing correction information derived from the spectrum shape of a first signal reflected from reference reflectors placed at known depths of a reference medium; and
correction means for continuously correcting in a time domain the spectrum shape of a second signal reflected from the medium to be measured and continuously correcting the spectrum shape of the entire second signal by changing frequency components of the second signal, and continuously correcting change of intensity of the entire second signal by changing the gain characteristics of the second signal.

* * * * *

UNITED STATES PATENT AND TRADEMARK OFFICE
CERTIFICATE OF CORRECTION

PATENT NO. : 4,757,715

DATED : July 19, 1988

INVENTOR(S) : Miwa et al.

It is certified that error appears in the above-identified patent and that said Letters Patent is hereby corrected as shown below:

Col. 8, line 17, "uz(f)" should be --uz(t)--.

line 59, equation (5), "$\int_0 z$" should be --$\int_0^z$--.

Signed and Sealed this

Sixth Day of December, 1988

Attest:

DONALD J. QUIGG

Attesting Officer  Commissioner of Patents and Trademarks